US012692225B2

(12) United States Patent
Rautenberg et al.

(10) Patent No.: US 12,692,225 B2
(45) Date of Patent: Jul. 28, 2026

(54) PROCESS FOR PREPARING 3-METHYLTHIOPROPIONALDEHYDE

(71) Applicant: Evonik Operations GmbH, Essen (DE)

(72) Inventors: Stephan Rautenberg; Thorsten Merker, Erftstadt (DE); Michael Eicker, Bergisch Gladbach (DE); Bruno Krudewig, Bonn (DE); Haohao Zhu, Euskirchen (DE); Chiu Kee Cheung, Alzenau (DE)

(73) Assignee: Evonik Operations GmbH, Essen (DE)

( * ) Notice: Subject to any disclaimer, the term of this patent is extended or adjusted under 35 U.S.C. 154(b) by 690 days.

(21) Appl. No.: 18/004,129

(22) PCT Filed: Jul. 6, 2021

(86) PCT No.: PCT/EP2021/068650
§ 371 (c)(1),
(2) Date: Jan. 3, 2023

(87) PCT Pub. No.: WO2022/008505
PCT Pub. Date: Jan. 13, 2022

(65) Prior Publication Data
US 2023/0278951 A1 Sep. 7, 2023

(30) Foreign Application Priority Data

Jul. 8, 2020 (EP) ..................................... 20184707

(51) Int. Cl.
*C07C 319/18* (2006.01)
(52) U.S. Cl.
CPC ................................. *C07C 319/18* (2013.01)
(58) Field of Classification Search
USPC .......................................................... 568/41
See application file for complete search history.

(56) References Cited

U.S. PATENT DOCUMENTS

| | | | |
|---|---|---|---|
| 5,905,171 | A | 5/1999 | Hsu |
| 6,031,138 | A | 2/2000 | Hsu et al. |
| 6,320,076 | B1 | 11/2001 | Hsu et al. |
| 10,633,335 | B2 | 4/2020 | Hierold et al. |
| 11,014,878 | B2 | 5/2021 | Rautenberg et al. |
| 11,524,936 | B2 | 12/2022 | Hierold et al. |
| 2002/0173677 | A1 | 11/2002 | Hsu et al. |

FOREIGN PATENT DOCUMENTS

| | | |
|---|---|---|
| CN | 102796030 A | 11/2012 |
| JP | 56-53648 A | 5/1981 |
| WO | WO 97/00858 A1 | 1/1997 |

OTHER PUBLICATIONS

U.S. Appl. No. 18/004,129, filed Jan. 3, 2023, Stephan Rautenberg et al.
International Search Report issued Oct. 1, 2021 in PCT/EP2021/068650, filed on Jul. 6, 2021, 2 pages.

*Primary Examiner* — Ana Z Muresan
(74) *Attorney, Agent, or Firm* — Oblon, McClelland, Maier & Neustadt, L.L.P.

(57) ABSTRACT

A process for preparing 3-methylthiopropionaldehyde, by a) providing a liquid stream with methyl mercaptan and/or the hemi thioacetal formed from 3-methylthiopropionaldehyde and methyl mercaptan; b) providing an acrolein with a vapor stream, where the major part of the vapor stream is acrolein, and the pressure of the vapor stream is lower than atmospheric pressure; c) introducing the liquid stream with methyl mercaptan and/or the hemi thioacetal formed from 3-methylthiopropionaldehyde and methyl mercaptan of a) and the acrolein with a vapor stream of b) into a reaction unit with a vapor-liquid mixing device, and d) reacting acrolein with methyl mercaptan and/or the hemi thioacetal formed from 3-methylthiopropionaldehyde and methyl mercaptan in the reaction unit of c) to give a 3-methylthiopropionalde-hyde product mixture.

20 Claims, 3 Drawing Sheets

Figure 1:
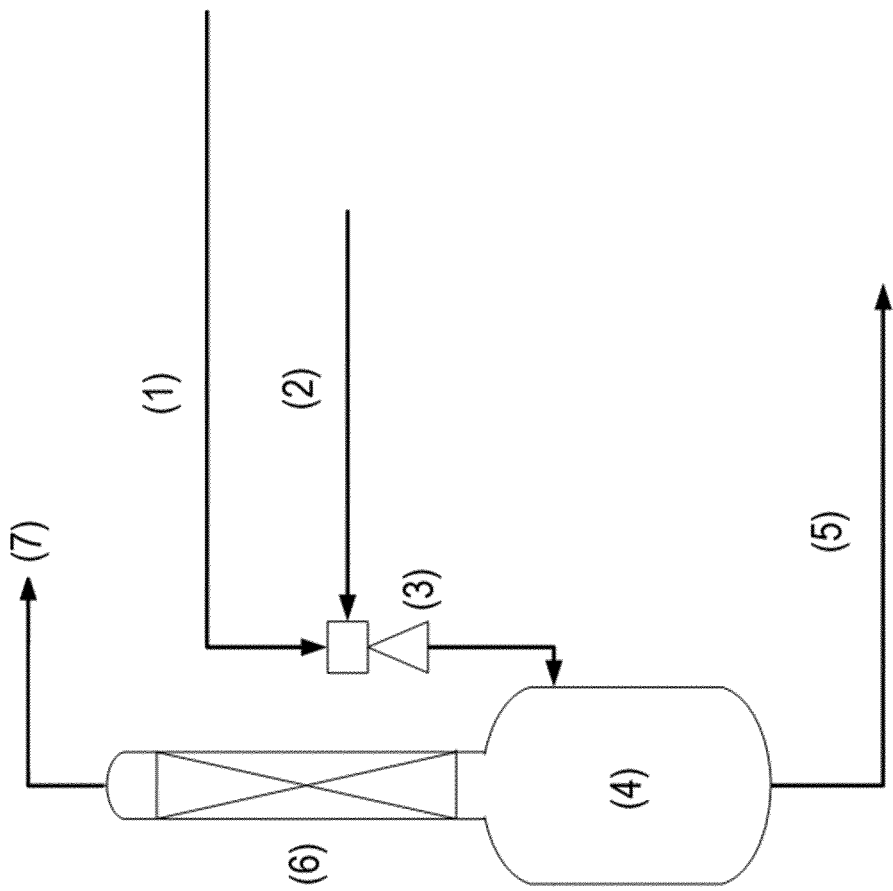

Figure 3:

Figure 3:
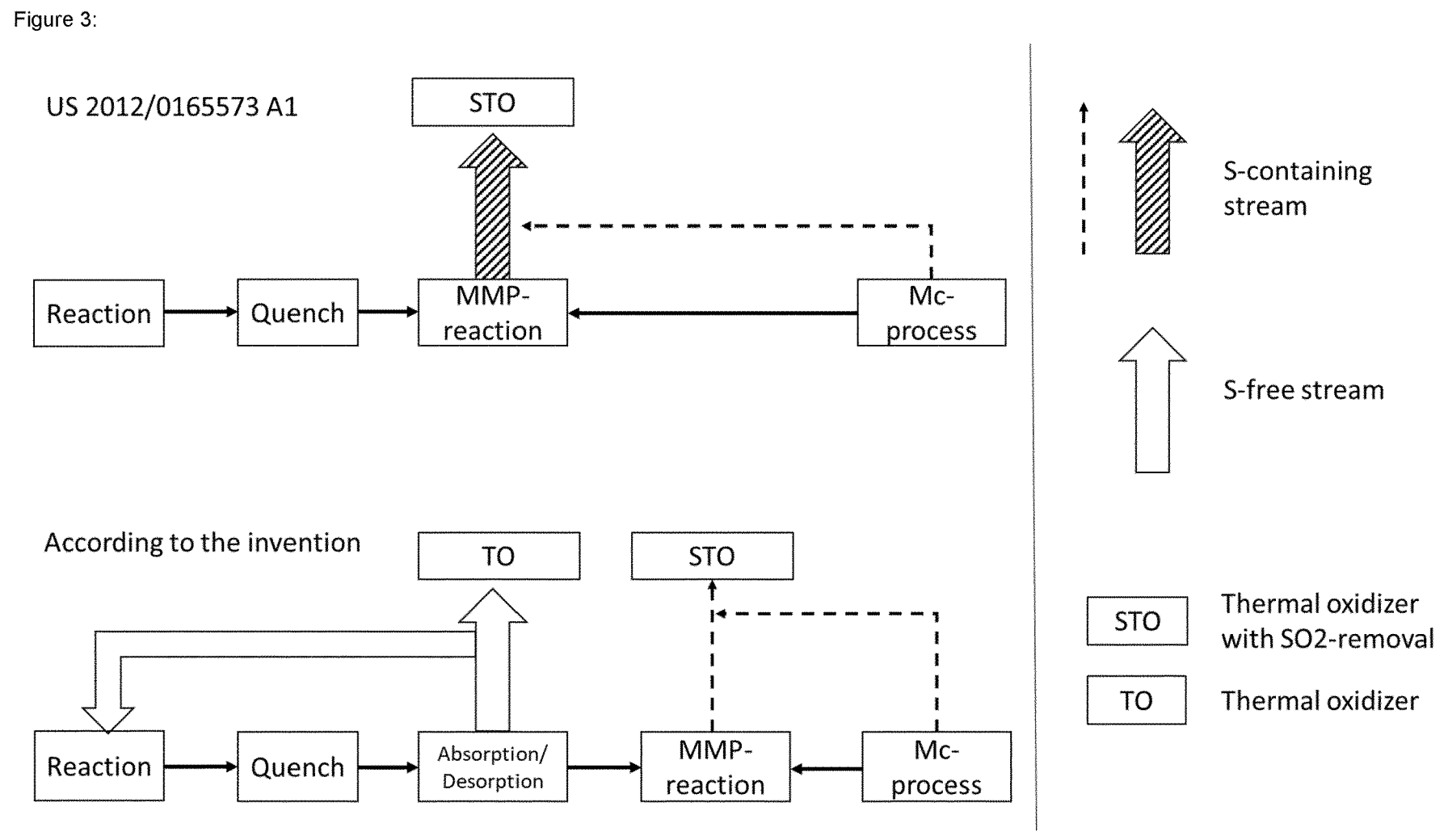

US 2012/0165573 A1

Reaction → Quench → MMP-reaction → STO

MMP-reaction ⇢ Mc-process

Mc-process → MMP-reaction (S-containing stream)

According to the invention

Reaction → Quench → Absorption/Desorption → MMP-reaction → Mc-process

Absorption/Desorption → TO

MMP-reaction ⇢ STO

Mc-process ⇢ MMP-reaction

S-containing stream

S-free stream

Thermal oxidizer with SO2-removal    STO

Thermal oxidizer    TO

PROCESS FOR PREPARING 3-METHYLTHIOPROPIONALDEHYDE

CROSS REFERENCE TO RELATED APPLICATIONS

This application is a National Stage entry under 35 U.S.C. § 371 of PCT/EP2021/068650, filed on Jul. 6, 2021, and claims priority to European Patent Application No. 20184707.6, filed on Jul. 8, 2020, the entire contents of which are incorporated herein by reference.

The present invention relates to a process for the preparation of 3-methylthiopropionaldehyde.

3-Methylthiopropionaldehyde, also known by the abbreviation MMP for methylmercaptopropionaldehyde or by the name 4-thiapentanal (UN number 2785), is an important intermediate in the production of D,L-methionine and its hydroxy analogue 2-hydroxy-4-methylthiobutyric acid, also known by the abbreviation MHA for methionine hydroxy analogue. Typically, 3-methylthiopropionaldehyde is prepared by reacting acrolein with methyl mercaptan in a Michael addition reaction.

The U.S. Pat. No. 4,225,516 discloses a two-stage process for the preparation of 3-methylthiopropionaldehyde (MMP), wherein in the first stage, the acrolein is absorbed from a gas mixture in MMP and, in the second stage, the acrolein dissolved in MMP is reacted with methyl mercaptan, which is continuously added to this reaction, at temperatures between 10 and 50° C. in the presence of a catalyst. In the absorption step a feed stream of liquid MMP is introduced at the head of an absorption column with a temperature ranging from about 0 to about −15° C., and said MMP feed stream is contacted in counter-current with an acrolein-containing vapor stream having a temperature in the range from about 0 to −5° C. However, the process of U.S. Pat. No. 4,225,516 has several drawbacks. First, MMP must be recycled at very low temperatures. This, however, leads to several disadvantages. First, the optimum reaction temperature for the formation of MMP from acrolein and methyl mercaptan is between 60 to 90° C., see for example US 2014/005437 A1, and thus higher than the reaction temperature applied in the process of U.S. Pat. No. 4,225,516. However, it would require significantly more energy in the process of U.S. Pat. No. 4,225,516, if the MMP was produced at a temperature between 60 to 90° C. and then recycled at a temperature between 0 and −15° C. Hence, the residence time must be significantly increased in the process of U.S. Pat. No. 4,225,516, in order to produce MMP in a sufficient yield at the relatively low reaction temperatures of this process. A further disadvantage of recycling MMP at a temperature of from about 0 to about −15° C., is the freezing of water still contained in the acrolein comprising vapor introduced into the reaction. The thus formed ice will either lead to blockages of the lines in the process or it will absorb a considerable amount of evaporation heat in the following MMP reaction, which makes the already bad energy balance of the process of U.S. Pat. No. 4,225,516 even worse. As mentioned in U.S. Pat. No. 4,225,516, a typical vapor stream from the preparation of acrolein contains 48.2 mol-% of water. Accordingly, the typical process condition of U.S. Pat. No. 4,225,516, lead to large amounts of wastewater and hence to high treatment/disposal costs. Therefore, the process of U.S. Pat. No. 4,225,516 is rather unattractive from an economic point of view.

The published patent application US 2012/0165573 A1 discloses a process for the preparation of MMP, in which acrolein which is obtained by the partial gas phase oxidation of propene first passes through a quench/by-product removal step, then is absorbed in MMP and reacts with free methyl mercaptan or with methyl mercaptan released from the hemi thioacetal of 3-methylthiopropionaldehyde and methyl mercaptan MMP. However, the off-gas from this process contains large amounts of organic sulfur compounds, such as MMP and methyl mercaptan, which are poisonous for the catalyst used in the acrolein preparation. Hence, said off-gas cannot be recycled back into the acrolein forming step. Due to environmental regulations, either the sulfur containing off-gas must be fed to a desulfurization step before being burnt in the thermal oxidizer or its combustion gas must be fed to desulfurizing step after the thermal oxidizer. This, however, leads to significant investment and operating costs, which make the process of US 2012/0165573 A1 rather unattractive from an economical view.

The published patent application US 2014/0005437 A1 also discloses a process for the preparation of MMP. In this process, first, (A) a mixture of propene and inert diluent gases is oxidized with air to give an oxidation reaction gas mixture comprising acrolein and by-products, which is (B) subsequently quenched to obtain a gas stream comprising acrolein and a quench liquid comprising residual acrolein and by-products. Next, (C) acrolein is recovered by stripping from the quench liquid in a lower portion of the quench and the stripped acrolein is returned to the quench. (D) A first portion of the gas stream comprising acrolein from the quench is absorbed in water to obtain an aqueous acrolein solution and a non-condensable gaseous stream comprising inert gases. (D1) At least a portion of said non-condensable gaseous stream is recycled to the propene oxidation to supply a gas, which reduces the oxygen concentration in the feed gas of the acrolein reaction. Then, (E) acrolein is distilled from the aqueous acrolein solution of the absorption step to obtain an acrolein-free aqueous bottom product and (E1) the thus obtained distilled acrolein is condensed. (F) The thus obtained condensed acrolein and a second portion of the gas stream comprising acrolein from the quench are reacted with methyl mercaptan in a mixture comprising at least one of 3-methylthiopropionaldehyde and the hemi thioacetal of methyl mercaptan and 3-methylthiopropionaldehyde to obtain the desired 3-methylthiopropionaldehyde. However, several disadvantages are associated with the process of US 2014/0005437 A1. First, the step (D) of absorbing a quenched acrolein comprising gas stream in water and the step (E) of distilling acrolein from the thus obtained aqueous acrolein solution have the severe disadvantage that an acrolein comprising liquid stream is generated. Acrolein and in particular liquid acrolein is amongst the chemicals with one of the highest risk potential. However, the acrolein comprising liquid stream of US 2014/0005437 A1 is not immediately further processed to a different compound with a lower risk potential. Therefore, the handling of said acrolein comprising liquid stream sets high standards to safety measures for the process of US 2014/0005437 A1. In addition, acrolein in liquid form is very susceptible to polymerization and therefore, a stabilizer must be added to the acrolein comprising liquid stream. Further, the off-gas from the MMP forming reaction still contains sulfur containing compounds and therefore must be fed to a desulfurization before thermal oxidation or the combustion gas of the off-gas must be fed to a desulfurization after thermal oxidation. However, desulfurization and thermal oxidation of the off-gas from the MMP forming reaction of US 2014/0005437 A1 is rather expensive because of the large volume of said off-gas stream.

Therefore, there was a need for a process for preparing 3-methylthiopropionaldehyde, which does not involve a condensation of acrolein, and whose off-gas has a significantly reduced content of sulfur containing compounds in comparison to the processes of the prior art.

It was found that this need is met by using an acrolein comprising vapor stream, whose major part is acrolein, and whose pressure is lower than atmospheric pressure, and introducing said acrolein comprising vapor stream and a liquid stream comprising methyl mercaptan (MC) and/or the hemi thioacetal (MMP-MC) formed from 3-methylthiopropionaldehyde (MMP) and methyl mercaptan (MC) into a reaction unit by means of a vapor-liquid mixing device, where the acrolein and the methyl mercaptan and/or the hemi thioacetal formed from 3-methylthiopropionaldehyde and methyl mercaptan are reacted to give 3-methylthiopropionaldehyde.

Object of the present invention is therefore a process for preparing 3-methylthiopropionaldehyde, comprising the steps of a) providing a liquid stream (1) comprising methyl mercaptan and/or the hemi thioacetal formed from 3-methylthiopropionaldehyde and methyl mercaptan, b) providing an acrolein comprising vapor stream (2), wherein the major part of said stream is acrolein, and the pressure of said stream is lower than atmospheric pressure, c) introducing the liquid stream comprising methyl mercaptan and/or the hemi thioacetal formed from 3-methylthiopropionaldehyde and methyl mercaptan of step a) and the acrolein comprising vapor stream of step b) into a reaction unit (4) by means of a vapor-liquid mixing device (3), and d) reacting acrolein with methyl mercaptan and/or the hemi thioacetal formed from 3-methylthiopropionaldehyde and methyl mercaptan in the reaction unit (4) of step c) to give a 3-methylthiopropionaldehyde comprising product mixture.

The MMP-forming process according to the technical teaching of US 2012/0165573 A1 gives an off-gas of ca. 7400 kg/h per ton of acrolein, that contains ca. 50 kg/h of sulfur containing components per ton of acrolein. Therefore, this off-gas must be treated in a thermal oxidizer with SO$_2$-removal (STO), which is very elaborate. By comparison, the MMP-forming process according to the present invention gives an off-gas of only ca. 0.8 kg/h per ton of acrolein, that contains only ca. 0.050 kg/h of sulfur containing components per ton of acrolein. Hence, the off-gas from the process according to the present invention must also be treated in a thermal oxidizer with SO$_2$-removal (STO). However, the off-gas from the process according to the present invention is not only just 0.1% or one one-thousandth of the off-gas of US 2012/0165573 A1. More importantly, compared with the off-gas of US 2012/0165573 A1, the off-gas from the process according to the present invention also contains just 0.1% or one one-thousandth of the off-gas of US 2012/0165573 A1. Hence, the amount of sulfur containing components in this off-gas is significantly reduced, compared to US 2012/0165573 A1. This is also illustrated in FIG. 3, where the upper presentation represents the process according to US 2012/0165573 A1 and the lower presentation represents the process according to the present invention. The process according to US 2012/0165573 A1 gives a rather large sulfur containing off-gas stream, while the process according to the present invention gives a significantly smaller sulfur containing off-gas stream. As a result of this, the treatment of this off-gas is also much less elaborate than it is for the off-gas of the process of US 2012/0165573 A1.

A further benefit of the process according to the present invention is that it allows an absorption/desorption in the acrolein forming process part prior to the MMP forming reaction. The thus released off-gas contains non-condensable gases which can be recycled to the acrolein forming reaction, where they allow to reduce the oxygen partial pressure below a safety threshold. Therefore, only the remaining non-condensable gases of the off-gas of the process according to the present invention must be fed to a simple thermal oxidizer. By comparison, the process of US 2012/0165573 A1 does not allow for such an absorption/desorption step. Therefore, it contains large amounts of organic sulfur compounds, such as MMP and methyl mercaptan, which are poisonous for the catalyst used in the acrolein forming process. Hence, said off-gas cannot be recycled back into the acrolein forming step. Rather, the total off-gas resulting from the process of US 2012/0165573 A1 must be fed to a thermal oxidizer with SO$_2$-removal (STO). This, however, makes the process of US 2012/0165573 A1 with respect to investment and operation costs.

The use of an acrolein comprising vapor stream has the advantage that the presence of liquified acrolein is avoided or at least significantly in the process according to the present invention. This has the benefit that the acrolein is immediately reacted with methyl mercaptan and/or the hemi thioacetal formed from 3-methylthiopropionaldehyde and methyl mercaptan to give 3-methylthiopropionaldehyde in step d). Hence, in contrast to the processes of the prior art, there is no liquified highly concentrated acrolein in the process according to the present invention. Rather, if acrolein is present in the liquid phase at all, its concentration in the liquid phase is rather low, specifically less than 10 wt.-%.

Further, the use of an acrolein comprising vapor stream has the general advantage that in case of a leakage of the process plant for preparing MMP no liquid acrolein is exposed to the environment, which in comparison to gaseous acrolein has a significantly higher risk potential. The use of an acrolein comprising vapor stream with a pressure, which is lower than atmospheric pressure, has the further advantage that any release of acrolein from the process plant for preparing MMP in case of a leakage of said plant is avoided or at least significantly reduced.

According to step c) of the process according to the present invention, the liquid stream (1) provided in step a) and the vapor stream (2) provided in step b) are introduced into a reaction unit by means of a vapor-liquid mixing device. This means that the two streams are contacted and mixed in the vapor-liquid mixing device (3) prior to the introduction into the reaction unit (4), i.e. the two streams are mixed in step c).

In principle, the reaction unit of step c) is not subject to any limitation and therefore be any type of reaction unit suitable for preparing 3-methylthiopropionaldehyde from acrolein and methyl mercaptan, e.g. a continuously stirred tank reactor (CSTR), a series of CSTRs, or a plug flow reactor. Nevertheless, it is preferred that said reaction unit is continuously stirred tank reactor (CSTR) because it allows for a residence time which is sufficiently long for a high conversion of the reactants and a high yield of 3-methylthiopropionaldehyde. The 3-methylthiopropionaldehyde comprising product mixture obtained in step d) is then withdrawn from the reaction unit (4) as 3-methylthiopropionaldehyde comprising stream (5).

In the context of the present invention the term the major part of said stream is acrolein is used as known to the skilled person and denotes that the acrolein comprising vapor stream provided in step b) contains more than 50 wt.-% of acrolein.

The higher the content of acrolein in the acrolein comprising vapor stream provided in step b) the better it is. Specifically, the higher the content of acrolein in the acrolein comprising vapor stream provided in step b), the faster the MMP forming reaction of step d) proceeds. Preferably, the acrolein comprising vapors stream of step b) contains at least 55 wt.-%, at least 60 wt.-%, at least 65 wt.-%, at least 70 wt.-%, at least 75 wt.-%, at least 80 wt.-%, at least 85 wt.-%, at least 90 wt.-%, at least 95 wt.-% or in an extreme case 100 wt.-% of acrolein.

In an embodiment of the process according to the present invention the acrolein comprising vapors stream of step b) contains at least 70 wt.-% of acrolein.

In the context of the present invention the term lower than atmospheric pressure is used as known to the skilled person and denotes any pressure under 1,013.25 hPa absolute (or 1,013 mbara). As far as the pressure within the process is concerned, the term lower than atmospheric pressure is used as known to the skilled person and denotes any absolute pressure under 1,013 mbara. In the context of the present invention the term bara or mbara is used as known to the skilled person and denotes the absolute pressure, which is zero-referenced against a perfect vacuum, using an absolute scale so it is equal to gauge pressure plus atmospheric pressure. Hereinafter, the term lower than atmospheric pressure is also used equivalent to reduced pressure.

In another embodiment of the process according to the present invention the pressure of the acrolein comprising vapors stream of step b) ranges from 300 to 950 mbara.

In principle, the process according to the present invention is not limited regarding the provision of acrolein comprising vapor stream with the major part of said stream being acrolein, provided the thus provided acrolein comprising vapor stream give the benefits of the present invention. For example, said acrolein comprising vapor stream can be a process comprising the steps i) feeding an aqueous acrolein solution, optionally devoid of gas which is difficult to condense, to a distillation column equipped with at least one re-boiler at its base and with at least one condenser at its top, ii) withdrawing a liquid mixture essentially comprising water at the base of said distillation column, iii) withdrawing a gas mixture essentially comprising acrolein and water at the top of the distillation column, iv) cooling the gas mixture of step iii) in the condenser to a temperature which makes it possible to obtain, on the one hand, an aqueous condensate, and on the other hand, a gas mixture enriched in acrolein, and v) withdrawing acrolein from the acrolein-rich gas mixture of step iv).

However, the acrolein comprising gas stream withdrawn from step v) may still contain varying amounts of water, which can condense during the process of the present invention.

It is therefore preferred to provide the acrolein comprising vapor stream by the following process for the purification of acrolein, comprising the steps of b1) splitting a liquid feed stream comprising acrolein into at least a first liquid stream and a second liquid stream, b2) introducing the first liquid stream with a temperature T1 into a distillation column at a point between the top and the bottom of the distillation column, b3) introducing the second liquid stream with a temperature T2 into the distillation column at the top of the distillation column, b4) withdrawing an overhead vapor stream enriched in acrolein from the distillation column, and withdrawing a bottom stream depleted in acrolein from the distillation column, wherein the temperature T2 of the second liquid stream in step c) is lower than the temperature T1 of the first liquid stream (2) in step b), and wherein the process for the purification of acrolein is performed under reduced pressure, preferably at a pressure from 300 to 950 mbara.

In another embodiment of the process according to the present invention the step c) comprises mixing the liquid stream comprising methyl mercaptan and/or the hemi thio-acetal formed from 3-methylthiopropionaldehyde and methyl mercaptan of step a) and the acrolein comprising vapor stream of step b) in the vapor-liquid mixing device of step c). Preferably, the methyl mercaptan and/or hemi thio-acetal comprising liquid stream of step a) and the acrolein comprising vapor stream of step b) are simultaneously introduced into the vapor-liquid mixing device of step c) in order to allow the best possible mixing of the two streams.

In principle the process according to the present invention is not subject to any limitation regarding the vapor-liquid mixing device of step b). Therefore, any conceivable vapor-liquid mixing device can be used in step b), provided it is compatible with the specific conditions of the process according to the present invention, and it is suitable to achieve the effects of the process according to the present invention. For example, the vapor-liquid mixing device in step b) can be a static or dynamic mixing device, specifically, a mixing device with mechanical agitation or without a mechanical agitation. Examples for a mixing device with mechanical agitation are agitated line mixers, agitated vessels, and rotating impellers. Examples for a mixing device without mechanical mixing are jet mixers, injectors, orifices and mixing nozzles, and packed tubes. A suitable vapor-liquid mixing device can also provide for the required pressure of the acrolein comprising vapor stream of step b) to be lower than at atmospheric pressure. Preferably, the reduced pressure of step b), i.e. being lower than atmospheric pressure, can be generated in the vapor-liquid mixing device of step c). For example, a jet mixer can be used, into which the methyl mercaptan and/or hemi thioacetal comprising liquid stream is introduced. The flow of said methyl mercaptan and/or hemi thioacetal comprising liquid stream generates the reduced pressure of the acrolein comprising vapor stream of step b). In addition to or in alternative, the reduced pressure of step b) can also be generated by a suitable device, for example a vacuum pump, downstream of the reaction unit of step c).

In a further embodiment of the process according to the present invention, the pressure of the acrolein comprising vapor stream of step b) is generated in the vapor-liquid mixing device of step c) and/or by a vacuum generating device downstream of the reaction unit of step c).

The reaction of acrolein with methyl mercaptan and/or the hemi thioacetal formed from 3-methylthiopropionaldehyde and methyl mercaptan to give 3-methylthiopropionaldehyde proceeds in the liquid phase. It is therefore necessary, that acrolein is absorbed from the vapor phase of the vapor stream of step b) into the liquid phase of the liquid stream of step a). The absorption of acrolein from the vapor phase into the liquid phase is improved when acrolein has a low vapor pressure in the liquid phase. This has the effect of a decrease in the amount of acrolein evaporating from the liquid phase. Since the vapor pressure of a substance is a function of its temperature and its concentration, it is therefore preferred that the acrolein comprising vapor stream of step b) has a low temperature. On the other side, the reaction of step d), where acrolein reacts with methyl mercaptan to give 3-methylthiopropionaldehyde, gives acceptable yield only at higher temperatures. Both conditions are met, when the temperature in step d) is high enough for the reaction to MMP and the concentration of acrolein in the liquid phase is low enough to limit the vapor pressure to the value of the pressure inside the MMP-reactor. For a pressure of 600 mbar, the condensation temperature of acrolein in the vapor stream is 38° C. For a temperature of 50° C. and a pressure of 600 mbar the acrolein concentration should be not more than of 50%, for a temperature of 90° C. not more than 11%. For a pressure of 800 mbar, the condensation temperature of acrolein in the vapor stream is 46° C. For a temperature of 50° C. and a pressure of 800 mbar the acrolein concentration should be not more than of 78%, for a temperature of 90° C. not more than 16%.

In an embodiment of the process according to the present invention the temperature in step d) is higher than the condensation temperature of acrolein in the vapor stream of step b).

Preferably, the temperature in step d) is in the range from 50 to 90° C., which gives very good yields for 3-methylthiopropionaldehyde. In particular, the temperature in step d) is in the range from 60 to 80° C., which is considered to be the optimum reaction temperature for the MMP forming reaction of step d).

As explained above, it is beneficial when the temperature in step d) is higher than the condensation temperature of acrolein in the vapor stream of step b). Considering the condensation temperature of acrolein in the preferred pressure range from 300 to 950 mbara, it is therefore preferred that the temperature of the acrolein comprising vapor stream in step b) ranges from 20 to less than 50° C., and in particular from 20 to 40° C.

In a further embodiment of the process according to the present invention the temperature of the acrolein comprising vapor stream in step b) ranges from 20 to less than 50° C.

Preferably, the temperature of the methyl mercaptan and/or the hemi thioacetal formed from 3-methylthiopropionaldehyde and methyl mercaptan comprising liquid stream in step d) ranges from 50 to 90° C., and the temperature of the acrolein comprising vapor stream in step b) ranges from 20 to less than 50° C.

According to the present invention, a methyl mercaptan and/or hemi thioacetal formed from 3-methylthiopropionaldehyde and methyl mercaptan comprising liquid stream is provided in step a) and introduced into the reaction unit of step c), where the methyl mercaptan and/or the hemi thioacetal formed from 3-methylthiopropionaldehyde and methyl mercaptan, contained in said liquid stream, reacts with acrolein to give 3-methylthiopropionaldehyde. In principle, the process according to the present invention is not subject to any limitation regarding the concentration of methyl mercaptan and/or hemi thioacetal in the liquid stream of step a). Therefore, the methyl mercaptan and/or hemi thioacetal comprising liquid stream of step a) can have any conceivable concentration of methyl mercaptan and/or hemi thioacetal. Nevertheless, it is preferred that the major part of the methyl mercaptan and/or hemi thioacetal comprising liquid stream is methyl mercaptan and/or hemi thioacetal. Hence, it is preferred that the methyl mercaptan and/or hemi thioacetal comprising liquid stream of step a) contains more than 50 wt.-% of methyl mercaptan and/or hemi thioacetal.

Preferably, the methyl mercaptan and/or hemi thioacetal comprising liquid stream of step a) contains at least 55 wt.-%, at least 60 wt.-%, at least 65 wt.-%, at least 70 wt.-%, at least 75 wt.-%, at least 80 wt.-%, at least 85 wt.-%, at least 90 wt.-%, at least 95 wt.-% or in an extreme case 100 wt.-% of methyl mercaptan and/or hemi thioacetal. One might expect that a methyl mercaptan and/or hemi thioacetal concentration as high as possible would be beneficial for a high yield of 3-methylthiopropionaldehyde in the reaction of step d). However, one has to consider the condensation heat released by the absorption of acrolein from the gas phase into the liquid phase and the reaction heat released in the MMP forming reaction, which lead to an increase in the reaction mixture of step d). This, however, would favor a vaporization of acrolein and methyl mercaptan from the liquid phase. Since the reaction of acrolein with methyl mercaptan and/or hemi thioacetal to 3-methylthiopropionaldehyde proceeds in the liquid phase, any vaporization of a reactant from the liquid into the vapor phase would lead to a loss in yield for 3-methylthiopropionaldehyde. Alternatively, one might expect that it would be beneficial to cool the methyl mercaptan and/or hemi thioacetal comprising liquid stream of step a) to a temperature which compensates for the temperature increase in step c) and/or d), in particular step d), caused by condensation and reaction heat, However, this would require a large cooling energy and in the worst case, one also had to heat the reaction mixture in step d) to the optimum temperature range for the MMP forming reaction. It is therefore beneficial when the methyl mercaptan and/or hemi thioacetal comprising liquid stream of step a) also comprises a solvent having a boiling point which is at least 20° C. higher than the boiling points of acrolein, i.e. a solvent with a boiling point of at 53° C. at a pressure of 1,013 mbar. A solvent with this feature can absorb condensation and reaction heat quite well and thus avoid or at least significantly reduce the evaporation of a volatile reactant from the liquid phase into the vapor phase. Preferably, said solvent has a boiling temperature in the range from 73 to 200° C., 73 to 190° C., 73 to 180° C. or 73 to 170° C.

In one embodiment of the process according to the present invention the methyl mercaptan and/or hemi thioacetal formed from 3-methylthiopropionaldehyde and methyl mercaptan comprising liquid stream of step a) also comprises a solvent having a boiling temperature which is at least 20° C. higher than the boiling temperature of acrolein.

In another embodiment the step a) of the process according to the present invention further comprises the steps a') mixing a methyl mercaptan and/or hemi thioacetal formed from 3-methylthiopropionaldehyde and methyl mercaptan comprising fluid stream with a solvent having a boiling temperature which is at least 20° C. higher than the boiling temperature of acrolein to provide the methyl mercaptan comprising liquid stream of step a).

Notwithstanding the specific temperatures and the additional presence of a solvent in the streams in steps a) and/or b), it may still happen that a part of the acrolein and/or methyl mercaptan evaporates from the liquid phase to the vapor phase, which would lead to a loss in yield for 3-methylthiopropionaldehyde. To keep said loss as low as possible, it is therefore beneficial to scrub the acrolein and/or methyl mercaptan, if contained in the off-gas from the reaction of step d), with a solvent having a boiling temperature which is at least 20° C. higher than the boiling temperature of acrolein, and to feed the thus obtained liquid stream containing acrolein and/or methyl mercaptan into step c) and/or d).

In a further embodiment the process according to the present invention further comprises the steps of e1) scrubbing acrolein and/or methyl mercaptan, if contained in the off-gas from the reaction of step d), with a solvent having a boiling temperature which is at least 20° C. higher than the boiling temperature of acrolein, to give an acrolein and/or methyl mercaptan comprising liquid stream, and e2) feeding the acrolein and/or methyl mercaptan comprising liquid stream obtained in step e1) to step c) and/or to step d).

In addition to or in alternative to said embodiment, it is also conceivable to scrub the vapor phase in the reaction unit (4) with a solvent having a boiling temperature which is at least 20° C. higher than the boiling temperature of acrolein. In that case any methyl mercaptan and/or acrolein which evaporated from the liquid phase into the vapor phase can be directly washed back/fed back into the reaction of step d).

A suitable solvent in the context of the process according to the present invention is 3-methylthiopropionaldehyde, i.e. MMP, and thus the reaction product itself, which has a boiling point of 165 to 166° C., at standard conditions, i.e. at a standard pressure of 1,013 mbar. The rather high boiling point and thus high heat absorption capacity of a 3-methylthiopropionaldehyde comprising stream have the effect of absorbing the condensation heat released upon mixing the liquid methyl mercaptan and/or hemi thioacetal comprising liquid stream with the gaseous acrolein and the reaction heat released upon the reaction of methyl mercaptan and/or hemi thioacetal with acrolein to give 3-methylthiopropionaldehyde. This effect avoids or significantly reduces the evaporation of any reactants from the liquid phase into the vapor phase. In addition, it is believed that methyl mercaptan reacts with 3-methylthiopropionaldehyde in an equilibrium reaction under formation of the corresponding hemi thioacetal of 3-methylthiopropionaldehyde, i.e. 1,3-bis(methylthio)-1-propanol. Said equilibrium reaction comprises the continuous incorporation of methyl mercaptan into 3-methylthiopropionaldehyde under formation of the corresponding hemi thioacetal of 3-methylthiopropionaldehyde and the continuous release of methyl mercaptan and 3-methylthiopropionaldehyde from said hemi thioacetal. It is therefore believed that a portion of methyl mercaptan is always present as free, i.e. unbound or not chemically bound, methyl mercaptan in this equilibrium and reacts with acrolein under formation of 3-methylthiopropionaldehyde. Simultaneous to the decrease of free methyl mercaptan in the equilibrium, further methyl mercaptan is released from the hemi thioacetal and available again for further reaction with acrolein to give 3-methylthiopropionaldehyde. Therefore, the use of 3-methylthiopropionaldehyde as a liquid solvent of the methyl mercaptan comprising stream and as solvent in the MMP forming reaction of step d) does not only improve the physical solubility but also the chemical solubility of methyl mercaptan in the liquid stream of step a). The high heat capacity and the dissolving properties of the 3-methylthiopropionaldehyde comprising stream are therefore believed to avoid or at least significantly reduce the evaporation of methyl mercaptan and acrolein upon the release of condensation and/or reaction heat.

In one embodiment of the process according to the present invention the methyl mercaptan and/or hemi thioacetal formed from 3-methylthiopropionaldehyde and methyl mercaptan comprising liquid stream of step a) also comprises a solvent, wherein said solvent is 3-methylthiopropionaldehyde.

In the easiest case, the solvent 3-methylthiopropionaldehyde is taken from the process according to the present invention, i.e. the 3-methylthiopropionaldehyde comprising product mixture obtained in step d), and then it is mixed with a stream comprising or consisting of methyl mercaptan to provide the methyl mercaptan comprising liquid stream (1). In order to provide for the best possible solubility of methyl mercaptan in the 3-methylthiopropionaldehyde, said 3-methylthiopropionaldehyde is tempered before being mixing with methyl mercaptan. In addition or as an alternative, it is also possible to recycle a part of the tempered 3-methylthiopropionaldehyde comprising stream in a bottom pump-around back to the reaction unit.

In another embodiment the process according to the present invention further comprises the steps f1) withdrawing a 3-methylthiopropionaldehyde comprising product mixture obtained in step d) as 3-methylthiopropionaldehyde comprising stream from the reaction unit, f2) feeding the complete or at least a part of the 3-methylthiopropionaldehyde comprising stream from step f1) to a heat exchanger to provide a tempered 3-methylthiopropionaldehyde comprising stream, and f3) feeding a part of the tempered 3-methylthiopropionaldehyde comprising stream of step f2) to the reaction unit (4) or mixing a part of the tempered 3-methylthiopropionaldehyde comprising stream of step f2) with methyl mercaptan and/or hemi thioacetal formed from 3-methylthiopropionaldehyde and methyl mercaptan to provide the methyl mercaptan and/or hemi thioacetal formed from 3-methylthiopropionaldehyde and methyl mercaptan comprising liquid stream (1).

In a preferred embodiment the 3-methylthiopropionaldehyde comprising stream is tempered in step f2) to a temperature in the range from 20 to 40° C.

In that case, the 3-methylthiopropionaldehyde comprising stream is particularly suitable for being mixed with methyl mercaptan and/or the hemi thioacetal formed from 3-methylthiopropionaldehyde and methyl mercaptan.

The 3-methylthiopropionaldehyde comprising product mixture obtained in step d), which is withdrawn as 3-methylthiopropionaldehyde comprising stream from the reaction unit and recycled back to the reaction unit and/or used as solvent for methyl mercaptan and/or the hemi thioacetal formed from 3-methylthiopropionaldehyde and methyl mercaptan, already contains MMP in a relatively high concentration. Therefore, said stream does not need to be purified before being recycled back to the reaction and/or before being used as solvent for methyl mercaptan. Rather, it is even preferred that said stream is not purified before being recycled and/or used as solvent, because the reaction can then be completed with respect to the unreacted acrolein, still contained in said stream.

In case the methyl mercaptan and/or the hemi thioacetal formed from 3-methylthiopropionaldehyde and methyl mercaptan comprising liquid stream of step a) contains a solvent which is different from 3-methylthiopropionaldehyde, the process according to the present invention further comprises the step of separating said solvent from the 3-methylthiopropionaldehyde comprising product mixture obtained from step d).

Most of the prior art processes use an at least equimolar ratio of methyl mercaptan to acrolein or a very small excess of methyl acrolein over acrolein in the preparation of 3-methylthiopropionaldehyde in order to avoid a polymerization of unreacted acrolein. These prior art processes involve the use of a liquified acrolein stream and of a liquid methyl mercaptan stream. While precise metering of a liquid stream can be easily carried out, it is not always possible to precisely meter a vapor stream. Accordingly, it is rather likely that the use of use an at least equimolar ratio of methyl mercaptan to acrolein or a very small excess of methyl acrolein over acrolein would lead to a (high) methyl mercaptan overdosing in the process according to the present invention. This, however, would lead to a waste of raw material. One could expect that the methyl mercaptan/acrolein ratio can be corrected subsequently. However, this does not make sense from an economic point of view.

In contrast to the prior art processes, the process according to the present invention therefore preferably involves an excess of acrolein over methyl mercaptan and/or the hemi thioacetal of methyl mercaptan and 3-methylthiopropional-dehyde with the possibility of adjusting said ratio by adding methyl mercaptan in a second reactor, downstream to the first reactor.

In yet another embodiment of the process according to the present invention the molar ratio methyl mercaptan and/or the hemi thioacetal of methyl mercaptan and 3-methylthio-propionaldehyde to acrolein in step c) and/or d) is less than 1.

Preferably, acrolein is present only in a small excess over methyl mercaptan and/or the hemi thioacetal of methyl mercaptan and 3-methylthiopropionaldehyde, i.e. 1,3-bis (methylthio)-1-propanol, in the process according to the present invention. Preferably, the molar ratio of acrolein to methyl mercaptan and/or 1,3-bis(methylthio)-1-propanol to acrolein ranges from 1.001 to 1.9, in particular from 1.001 to 1.8, from 1.001 to 1.007, from 1.001 to 1.6, from 1.001 to 1.5, from 1.001 to 1.4, from 1.001 to 1.3, from 1.001 to 1.2 or from 1.001 to 1.1.

If acrolein is still present in the 3-methylthiopropional-dehyde comprising stream (5) withdrawn from the reaction unit (4), the MMP forming reaction can then be completed (i) by recycling the complete or a part of said 3-methylth-iopropionaldehyde comprising stream (5) to the reaction and/or using it as solvent for methyl mercaptan and/or the hemi thioacetal formed from 3-methylthiopropionaldehyde and methyl mercaptan, as mentioned above, or (ii) by feeding the complete or a part of said 3-methylthiopropi-onaldehyde comprising stream (5) to a secondary reactor, downstream the reaction unit of step d). In option (ii), a methyl mercaptan and/or the hemi thioacetal formed from 3-methylthiopropionaldehyde and methyl mercaptan com-prising stream, which can be precisely metered, is then added to said 3-methylthiopropionaldehyde comprising stream. In order to complete the MMP forming reaction, it is here preferred to use an excess of methyl mercaptan and/or the hemi thioacetal formed from 3-methylthiopropi-onaldehyde and methyl mercaptan over acrolein.

The present invention is further illustrated by the follow-ing figures and examples.

FIGURES

Figure 2:
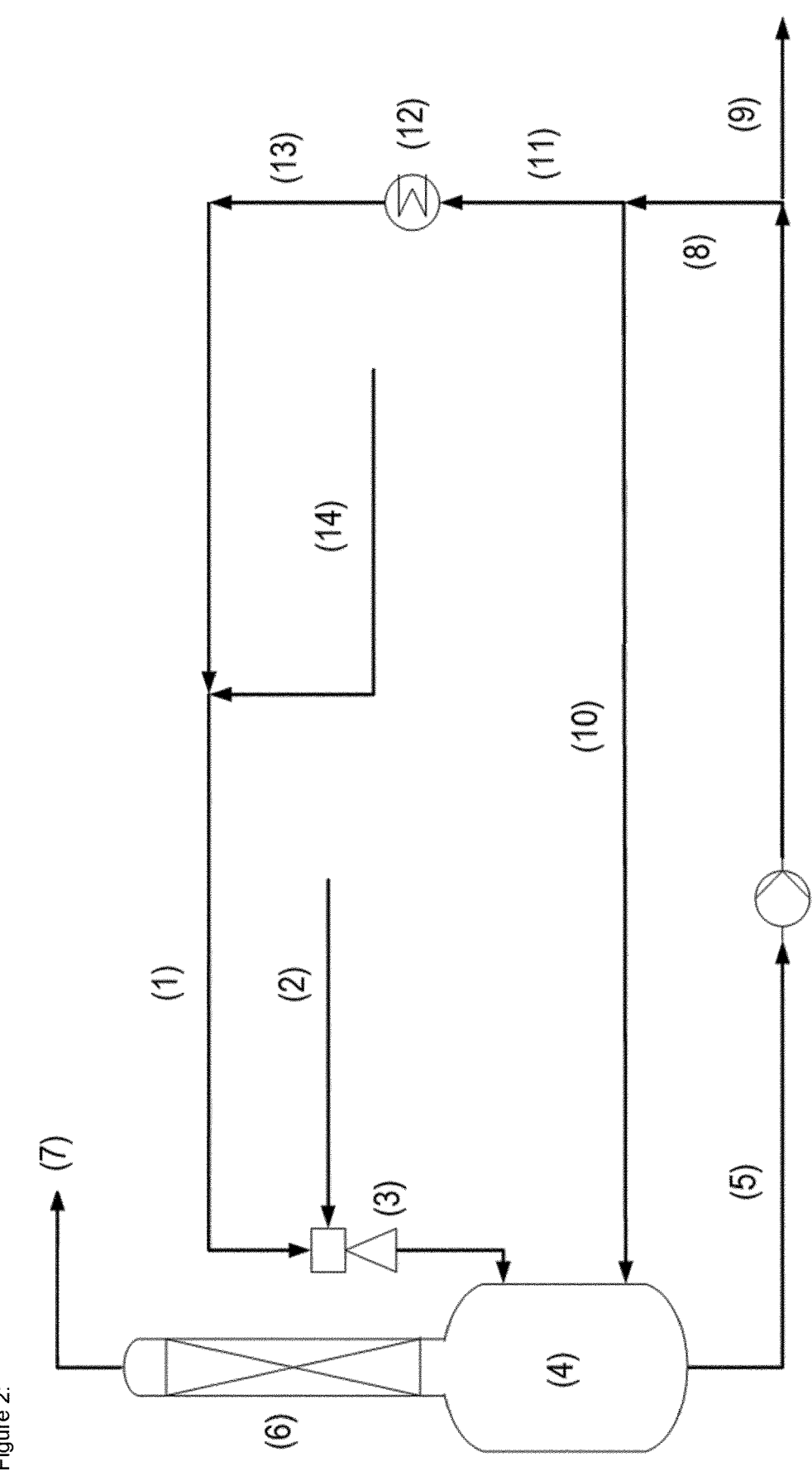

FIG. 1 shows a process according to the present invention, in which the numbers denote the following items (1) liquid stream comprising methyl mercaptan and/or the hemi thioacetal formed from 3-methylthiopropionalde-hyde and methyl mercaptan, (2) acrolein comprising vapor stream, (3) vapor-liquid mixing device, (4) reaction unit, (5) 3-methylthiopropionaldehyde comprising product stream, (6) scrubber, (7) off-gas stream FIG. 2 shows an embodiment of the process according to the present invention, in the meaning of the numbers (1) to (7) is identical with FIG. 1, and the additional numbers denote the following items (8) partial MMP recycle stream, (9) process MMP stream,

(10) bottom pump-around MMP recycle stream,

(11) partial MMP recycle stream,

(12) heat exchanger,

(13) cooled partial MMP recycle stream,

(14) liquid stream comprising methyl mercaptan and/or the hemi thioacetal formed from 3-methylthiopropi-onaldehyde and methyl mercaptan FIG. 3 shows a comparison between the process of the prior art, US 2012/0165573 A1, (above) and the process according to the present invention (below).

EXAMPLES

The examples herein are performed using a computational model of a process based on the individual processes of the examples. Process modelling is an established and reliable methodology used by engineers to simulate complex chemi-cal processes before building the real plant. In the context of the examples herein the commercial modelling software Aspen Plus® (Aspen Technology, Inc 20 Crosby Roads, Bedford, Massachusetts 01730, USA) was used in combi-nation with physical property data available from public databases.

1. Comparative Example

Using the modelling software Aspen Plus®, the prepara-tion of MMP is simulated for a production process according to the technical teaching of US 2012/0165573 A1: A stream of a gaseous mixture comprising acrolein is absorbed in a reactive absorber in a mixture of MMP, methyl mercaptan and the hemi thioacetal formed from 3-methylthiopropional-dehyde and methyl mercaptan, and then reacts with methyl mercaptan to give 3-methylthiopropionaldehyde.

MMP and reacts with free methyl mercaptan or with methyl mercaptan released from the hemi thioacetal formed from 3-methylthiopropionaldehyde and methyl mercaptan MMP. After being absorbed from the gas phase into the liquid phase, the absorbed acrolein reacts with methyl mer-captan and/or the hemi thioacetal formed from 3-methylth-iopropionaldehyde and methyl mercaptan to give MMP. The thus obtained MMP comprising liquid stream is withdrawn from the reaction unit and subjected to a purification to remove gaseous impurities and by-products. The process of said process gives an off-gas of ca. 7400 kg/h per ton acrolein with 50 kg/h of sulfur containing components per ton of acrolein, based on the data in Tables 1 and 4 of US 2012/0165573 A1. The specific composition of this off-gas and the flow rates of its components are given in Table 1 below.

TABLE 1

| composition of the off-gas in a simulation of the process according to US 2012/0165573 A1 | | |
|---|---|---|
| Components | Concentration [wt.-%] | Flow rate [kg/h per ton acrolein] |
| $CO_2$ | 1.064 | 78 |

TABLE 1-continued

| composition of the off-gas in a simulation of the process according to US 2012/0165573 A1 | | |
|---|---|---|
| Components | Concentration [wt.-%] | Flow rate [kg/h per ton acrolein] |
| CO | 0.368 | 27 |
| $O_2$ | 6.079 | 448 |
| Ar | 0.926 | 68 |
| $N_2$ | 89.891 | 6621 |
| propene | 0.254 | 19 |
| propane | 0.049 | 4 |
| $H_2O$ | 0.341 | 25 |
| acetaldehyde | 0.223 | 16 |
| acrolein | 0.000 | 0 |
| acetic acid | 0.014 | 1 |
| methyl mercaptan | 0.356 | 26 |
| dimethyl sulfide | 0.216 | 16 |
| dimethyl disulfide | 0.021 | 2 |
| MMP | 0.150 | 11 |
| methanol | 0.016 | 1 |
| dimethyl ether | 0.034 | 3 |
| $H_2S$ | 0 | 0 |
| Sum | 100 | 7366 |

2. Example According to the Invention

Using the modeling software Aspen Plus®, the preparation of MMP is simulated for a production process shown in FIG. 2: A methyl mercaptan (MC) comprising liquid steam (1), comprising ca. 82 wt.-% of the hemithioacetal of methyl mercaptan and MMP and ca. 3 wt.-% of $H_2O$, and an acrolein comprising vapor stream (2), having a pressure of ca. 0.60 bara and comprising ca. 92.6 wt.-% acrolein, ca. 2 wt.-% of acetaldehyde, and ca. 5 wt.-% water, are introduced into the reaction unit (4) by means of the vapor-liquid mixing device (3). In the reaction unit (4) acrolein is reacted with methyl mercaptan at a temperature of ca. 64° C. to give a 3-methylmercaptopropionaldehyde comprising product mixture. Compared to the process of US 2012/0165573 A1, the process of the present invention gives an off-gas of only ca. 0.8 kg/h per ton acrolein. In other words, the off-gas of the process according to the present invention is only 0.01% of the off-gas of the process of US 2012/0165573 A1. Further, said off-gas only contains 0.05 kg/h of sulfur containing components per ton acrolein, which is only 0.1% of the sulfur containing components in the off-gas of the process of US 2012/0165573 A1. The composition of the off-gas of a process according to the present invention and the flow rates of its components are given in the table 2 below.

TABLE 2

| composition of the off-gas in a simulation of the process according to the present invention | |
|---|---|
| Components | Flow rate [kg/h per ton acrolein] |
| $CO_2$ | 0.000 |
| CO | 0.007 |
| $O_2$ | 0.077 |
| Ar | 0.000 |
| $N_2$ | 0.605 |
| propene | 0.004 |
| propane | 0.003 |
| $H_2O$ | 0.026 |
| acetaldehyde | 0.022 |
| acrolein | 0.005 |

TABLE 2-continued

| composition of the off-gas in a simulation of the process according to the present invention | |
|---|---|
| Components | Flow rate [kg/h per ton acrolein] |
| acetic acid | 0.000 |
| methyl mercaptan | 0.000 |
| dimethyl sulfide | 0.008 |
| dimethyl disulfide | 0.000 |
| MMP | 0.007 |
| methanol | 0.000 |
| dimethyl ether | 0.012 |
| $H_2S$ | 0.011 |
| Sum | 0.788 |

The invention claimed is:

1. A process for preparing 3-methylthiopropionaldehyde, the process comprising:
   (a) providing a liquid stream comprising methyl mercaptan and/or a hemi thioacetal formed from 3-methylthiopropionaldehyde and methyl mercaptan;
   (b) providing a vapor stream comprising acrolein in major part, a pressure of the stream being lower than atmospheric pressure;
   (c) introducing the liquid stream from the providing (a) and the vapor stream from the providing (b) into a reaction unit with a vapor-liquid mixing device; and
   (d) reacting the acrolein with the methyl mercaptan and/or the hemi thioacetal formed from 3-methylthiopropionaldehyde and the methyl mercaptan in the reaction unit of the introducing (c) to give a product mixture comprising 3-methylthiopropionaldehyde.

2. The process of claim 1, wherein the vapor stream of the providing (b) comprises the acrolein in at least 70 wt. %.

3. The process of claim 1, wherein the pressure of the vapor stream of the providing (b) is in a range of from 300 to 950 mbara.

4. The process of claim 1, wherein the introducing (c) comprises mixing the liquid stream of the providing (a) and the vapor stream of the providing (b) in the vapor-liquid mixing device of the introducing (c).

5. The process of claim 1, wherein the pressure of the vapor stream of the providing (b) is generated in the vapor-liquid mixing device of the introducing (c) and/or by a vacuum generating device downstream of the reaction unit of the introducing (c).

6. The process of claim 1, wherein a temperature in the reacting (d) is higher than a condensation temperature of acrolein in the vapor stream of the providing (b).

7. The process of claim 1, wherein a temperature of the liquid stream in the reacting (d) is in a range of from 50 to 90° C.

8. The process of claim 1, wherein a temperature of the vapor stream in the introducing (b) is in a range of from 20 to less than 50° C.

9. The process of claim 1, wherein the liquid stream of the introducing (a) further comprises:
   a solvent having a boiling temperature which is at least 20° C. higher than a boiling temperature of acrolein.

10. The process of claim 1, further comprising:
   (e1) scrubbing acrolein and/or methyl mercaptan, if contained in an off-gas from the reaction of the reacting (d), with a solvent having a boiling temperature which is at least 20° C. higher than a boiling temperature of acrolein, to give a second liquid stream comprising acrolein and/or methyl mercaptan; and (e2) feeding the second liquid stream, obtained in the scrubbing (e1) to the introducing (c) and/or to the reacting (d).

11. The process of claim 1, wherein the liquid stream of the introducing (a) further comprises a solvent, and wherein the solvent is 3-methylthiopropionaldehyde.

12. The process of claim 1, further comprising:

(f1) withdrawing the product mixture obtained in the reacting (d) as a product stream, comprising 3-methylthiopropionaldehyde, from the reaction unit;

(f2) feeding at least a part of the product stream from the withdrawing (f1) to a heat exchanger to provide a tempered product comprising stream; and (f3) feeding a part of the tempered product stream from the feeding (f2) to the reaction unit or mixing a part of the tempered product stream from the feeding (f2) with methyl mercaptan and/or the hemi thioacetal formed from 3-methylthiopropionaldehyde and methyl mercaptan to provide the liquid stream.

13. The process of claim 12, wherein the product stream is tempered in the feeding (f2) to a temperature in a range from 20 to 40° C.

14. The process of claim 1, wherein, when the liquid stream of the providing (a) further comprises a solvent different from the 3-methylthiopropionaldehyde, the process further comprises:

separating the solvent from the product mixture obtained from the reacting (d).

15. The process of claim 1, wherein a molar ratio of the methyl mercaptan and/or the hemi thioacetal formed from methyl mercaptan and 3-methylthiopropionaldehyde to the acrolein in the introducing (c) and/or reacting (d) is less than 1.

16. The process of claim 1, wherein the pressure of the acrolein comprising vapor stream of the providing (b) ranges is in a range of from 300 to 800 mbara.

17. The process of claim 1, wherein the pressure of the acrolein comprising vapor stream of the providing (b) ranges is in a range of from 600 to 950 mbara.

18. The process of claim 1, wherein the pressure of the acrolein comprising vapor stream of the providing (b) ranges is in a range of from 300 to 600 mbara.

19. The process of claim 1, wherein the vapor stream of the providing (b) comprises the acrolein in at least 70 wt. %, and wherein the pressure of the vapor stream of the providing (b) is in a range of from 300 to 950 mbara.

20. The process of claim 1, wherein the vapor stream of the providing (b) comprises the acrolein in at least 70 wt. %, wherein the pressure of the vapor stream of the providing (b) is in a range of from 300 to 950 mbara, and wherein a temperature of the liquid stream in the reacting (d) is in a range of from 50 to 90° C.

* * * * *